United States Patent
Kalopissis et al.

[11] 3,948,596
[45] Apr. 6, 1976

[54] OXIDATION DYE FOR KERATINIC FIBERS CONTAINING 2-HALO-5-ACETAMINOPHENOL AS A COUPLER

[75] Inventors: Gregoire Kalopissis, Paris; Andree Bugaut, Boulogne-sur-Seine, both of France

[73] Assignee: Societe Anonyme dite: L'Oreal, Paris, France

[22] Filed: June 24, 1974

[21] Appl. No.: 482,560

[30] Foreign Application Priority Data
June 22, 1973  Luxemburg............................ 67861

[52] U.S. Cl. ............................ 8/10.2; 8/10; 8/10.1; 8/11; 8/32
[51] Int. Cl.² .......................................... A61K 7/13
[58] Field of Search ............. 260/558 A; 8/10.2, 11, 8/32

[56] References Cited
UNITED STATES PATENTS

| | | | |
|---|---|---|---|
| 3,337,411 | 8/1967 | Wilmsmann et al. .................. | 8/10.2 |
| 3,359,168 | 12/1967 | Brechner et al. ....................... | 8/10.2 |
| 3,415,608 | 12/1968 | Tucker................................. | 8/10.2 |
| 3,712,158 | 1/1973 | Kalopissis et al. ......................... | 8/11 |

OTHER PUBLICATIONS
Raiford et al., *J. Amer. Chem. Soc.*, Vol. 67, pp. 878–879, (1945).

*Primary Examiner*—Sam Rosen
*Assistant Examiner*—Vera C. Clarke
*Attorney, Agent, or Firm*—Cushmam, Darby & Cushman

[57] ABSTRACT

A dye composition for keratinic fibers comprising in combination:

a. at least one oxidation base selected from the group consisting of an aromatic or heterocyclic compound carrying either two amino groups or one amine group and one hydroxy group, fixed in para position relative to each other on the aromatic or heterocyclic nucleus of said compound, said oxidation base being in the form of a free base or in the form of an acid addition salt thereof; and b. at least one coupler of the formula:

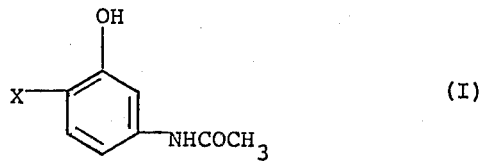

(I)

wherein X represents a member selected from the group consisting of F, Cl or Br.

15 Claims, No Drawings

OXIDATION DYE FOR KERATINIC FIBERS CONTAINING 2-HALO-5-ACETAMINOPHENOL AS A COUPLER

The invention also relates to a compound of the formula

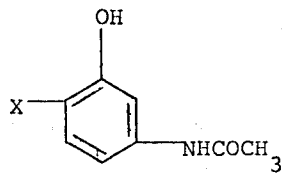

wherein X is Cl or F.

The use in dye compositions for keratinic fibers and especially for living human hair of paraphenylenediamines, paraaminophenols and even certain heterocyclic compounds, such as 2,5-diamino pyridine or 2-hydroxy-5-amino pyridine, is quite well known. These compounds are frequently designated as "oxidation bases" and are generally utilized in combination with compounds designated as "couplers".

These couplers react in an oxidizing medium with the oxidation bases to produce dyes which impart to the fibers or to living human hair a great variety of shades, depending upon the chemical structure of the two reactants. In general, the couplers are metadiamines, metaaminophenols, metadiphenols, metaacetylaminophenols, metaureidophenols, pyrazolones or even pyridine derivatives, such as 2,6-diamino pyridine.

The choice of the coupler is motivated not only by the shade desired, but also to a large extent by the degree of stability of the shade to light and to weather. For example, the progressive turning to red of the violet and blue shades obtained with paraphenylenediamines and metadiamines is quite well known as extremely inconvenient and highly undesirable phenomenon.

An object of the present invention is the provision of a dye composition for keratinic fibers and in particular for living human hair which overcomes the above noted disadvantages, said composition comprising in combination a. at least one oxidation base selected from the group consisting of an aromatic or heterocyclic compound carrying either two amino groups or an amino group and a hydroxy group, fixed in para position relative to each other on the aromatic or heterocyclic nucleus of said compound, said oxidation base being in the form of a free base or in the form of an acid addition salt thereof, b. and at least one coupler of the formula:

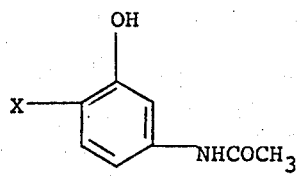

(I)

wherein X represents a member selected from the group consisting of F, Cl or Br. Preferably the aromatic nucleus is phenyl and the heterocyclic nucleus is pyridyl.

When as the oxidation base there is employed various paraphenylenediamines, the resulting dye composition provides very interesting green colorations which are stable to light and to weather. In effect the attainment of green in a capillary dye is quite desirable in order both to avoid the red coloration of hair and to diminish redness.

Representative paraphenylenediamines usefully employed as the oxidation base in the present invention include paraphenylenediamine, paratoluylenediamine, methoxyparaphenylenediamine, chloroparaphenylenediamine, 2,6-dimethyl paraphenylenediamine,
2,5-dimethylparaphenylenediamine,
2-methyl-5-methoxy paraphenylenediamine, 2,6-dimethyl-5-methoxy paraphenylenediamine,
N,N-dimethyl paraphenylenediamine, 3-methyl-4-amino-N,N-diethylaniline,
N,N-di-($\beta$-hydroxyethyl) paraphenylenediamine,
3-methyl-4-amino-N,N-di-($\beta$-hydroxyethyl) aniline,
3-chloro-4-amino-N,N-di-($\beta$-hydroxyethyl) aniline,
4-amino-N,N-(ethyl, carbamylmethyl) aniline,
3-methyl-4-amino-N,N-(ethyl, carbamylmethyl) aniline,
4-amino-N,N-(ethyl, $\beta$-piperidinoethyl) aniline,
3-methyl-4-amino-N,N-(ethyl, $\beta$-piperidinoethyl) aniline,
4-amino-N,N-(ethyl, $\beta$-morpholinoethyl) aniline,
3-methyl-4-amino-N,N-(ethyl, $\beta$-morpholinoethyl) aniline,
4-amino-N,N-(ethyl, $\beta$-acetylaminoethyl) aniline,
3-methyl-4-amino-N,N-(ethyl, $\beta$-acetylaminoethyl) aniline,
4-amino-N,N-(ethyl, $\beta$-mesylaminoethyl) aniline,
3-methyl-4-amino-N,N-(ethyl, $\beta$-mesylaminoethyl) aniline,
4-amino-N,N-(ethyl, $\beta$-sulfoethyl) aniline,
3-methyl-4-amino-N,N-(ethyl, $\beta$-sulfoethyl) aniline,
N-[(4'-amino) phenyl] morpholine, and
N-[(4'-amino) phenyl] piperidine.

These oxidation bases can be introduced in the dye composition in the form of a free base or in the form of an acid addition salt, for example in the form of the hydrochloride, the hydrobromide or the sulfate thereof.

The couplers of formula (I) utilized in combination with a second important class of oxidation bases, i.e. paraaminophenols also provide the advantage of giving, in the presence of an oxidizing agent, colors which are very stable to light and to weather. The dyes obtained are blond or light chestnut.

Representative paraaminophenols usefully employed in the present invention include: paraaminophenol, 2-methyl-4-aminophenol, 3-methyl-4-aminophenol, 2-chloro-4-aminophenol, 3-chloro-4-aminophenol, 2,6-dimethyl-4-aminophenol, 3,5-dimethyl-4-aminophenol, 2,3-dimethyl-4-aminophenol, and 2,5-dimethyl-4-aminophenol.

There can also be used with the couplers of formula (I) oxidation bases having a heterocyclic nucleus including 2,5-diamino pyridine and 2-hydroxy-5-aminopyridine.

All the oxidation bases can be used in the free form or in the form of salts, such as the hydrochloride, the hydrobromide and sulphate salt thereof.

The dye compositions according to the invention are characterized by the following essential features:

a. they must contain at least one of the compounds of the formula (I);
b. they must contain a paraphenylenediamine or a paraaminophenol or a heterocyclic oxidation base such as 2,5-diamino pyridine or 2-hydroxy-5-amino pyridine or their salts;
c. they can contain several couplers of formula (I);
d. they can contain, in addition to coupler (I) other known couplers such as: resorcin, metaaminophenol, 2,4-diamino anisole, 7-hydroxyphenomorpholine, 2-methyl-5-aminophenol, 2,6-dimethyl-5-aminophenol, 2-chloro-5-aminophenol, 3-amino-4-methoxyphenol, 2,6-dimethyl-5-ureidophenol, 3-acetylaminophenol, 2-methyl-5-ureidophenol, 2-methyl-5-acetylaminophenol, and the pyrazolones, as well as other couplers containing active methylene groups;
e. they can contain several oxidation bases;
f. they can also contain dyes in the form of leucoderivatives, in particular diphenylamines substituted in the 4 and 4' position by $NH_2$ or OH groups as well as other various substituents on the two benzene rings, which diphenylamines on oxidation produce indamines, indoanilines or indophenols;
g. they can aso contain direct dyes such as azo dyes, anthraquinones, nitrobenzene dyes, indamines, indoanilines, or indophenols; and
h. they can be utilized in the form of an aqueous or hydroalcoholic solution containing a lower alkanol, preferably ethanol or isopropanol.

The dye composition of the present invention can also contain other solvents such as glycols, for example butylglycol, monomethyl ester of diethylene glycol, etc., wetting or washing agents such as the sulfates of fatty alcohols, ethanolamides of fatty acids, polyoxyethylenated fatty alcohols and acids, thickening agents such as carboxymethylcellulose, higher fatty alcohols, cosmetic polymers such as the polymers and copolymers of vinyl pyrrolidone, polymers of acrylic acid, perfumes, antioxidants, sequestering agents, alkalizing agents, for example, ammonia, sodium phosphate, sodium carbonate, and alkanolamines, acidifying agents, for example, phosphoric acid, lactic acid and acetic acid.

The aggregate of the oxidation bases, couplers, dyes and leucoderivatives included in the composition, as defined above, represent from 0.3–7% by weight of the said composition.

The couplers can be used in an amount practically molar with respect to the oxidation bases. However, it is often advantageous to utilize an excess of the oxidation base, for example 4 to 5 moles of oxidation base per mole of coupler. This does not exclude, however, the use in certain cases of an excess of coupler with respect to the oxidation base. For example, 2 moles of coupler per mole of oxidation base can be used. Generally, the ratio of oxidation base : coupler is between about 10:1 and 1:2.5, preferably between 2.5:1 and 1:1.5 and more preferably about 1:1.

The concentration of the coupler compounds (I) can vary between 0.05–3.5% by weight of the total composition.

The pH of the dye compositions of the present invention can vary between 5 and 11 and preferably between 8 and 10.

The dye composition according to the present invention are used in a conventional manner. They are presented in the form of liquids of variable viscosity or in the form of creams.

After addition of an oxidizing agent to the composition, the resulting mixture is applied to the hair and is permitted to remain in contact therewith for a period of about 10 to 30 minutes, at a temperature between 15° and 30°C. Thereafter the hair is rinsed, washed and dried.

The oxidizing agent utilized is most often $H_2O_2$ although other oxidizing agents such as urea peroxide and persalts, for example, persulphates and perborates, can also be used.

The compositions according to the invention can also be packages in aerosol containers.

The present invention also relates to a new compound of formula (I):

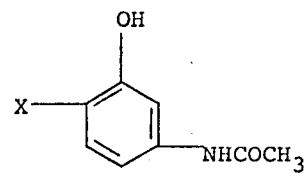

wherein X represents a member selected from the group consisting of fluorine and chlorine.

The following example illustrates the present invention. Unlss otherwise stated, all parts and percentages are by weight.

EXAMPLE A 2-chloro-5-acetaminophenol is prepared in accordance with the following reaction scheme:

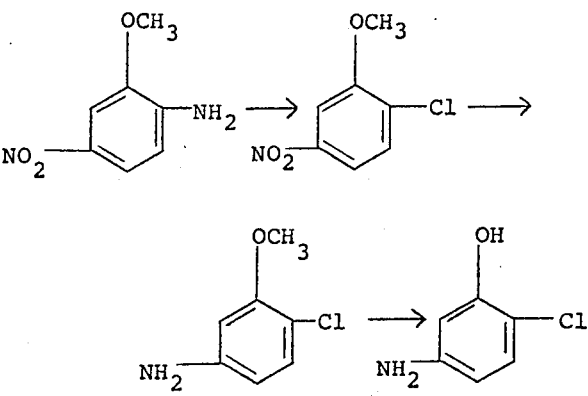

FIRST STEP

Preparation of 2-chloro-5-nitro anisole starting with 2-amino-5-nitro anisole by diazotization of the amine and decomposition of the diazonium salt in the presence of copper chloride.

One mole (168 grams) of 2-amino-5-nitro anisole is introduced into 1.68 liters of acetic acid. To the resulting solutinn, there is added little by little, with agitation and while maintaining the temperature at about 15°C, 1 mole (69 grams) of sodium nitrite in solution in 483 cc of concentrated sulfuric acid. The resulting solution of the diazonium salt is then filtered and after raising its temperature to about 95°C it is added over a period of 10 minutes to a hydrochloric solution of copper chloride obtained by dissolving 1.1 mole (218 grams) of $Cu_2Cl_2$ in 3.5 liters of hydrochloric acid ($d = 1.16$), which has previously been heated to 95°C. At the end of 15 minutes, the evolution of nitrogen ceases and the reaction mixture is cooled to 0°C. Thereafter the 2-chloro-5-nitro anisole (159 grams) which melts at 82°C is recovered from the reaction mixture by filtration.

SECOND STEP

Preparation of 2-chloro-5-amino anisole by reducing 2-chloro-5-nitro anisole.

1.23 Kilograms of powdered iron are introduced into 6.56 liters of water to which has been added 0.94 liter of acetic acid previously heated to 70°C. There are then added, little by little and with agitation, 5 moles (937.5 grams) of 2-chloro-5-nitro anisole. The addition is so controlled that the temperature of the reaction mixture is maintained at about 100°C. When the reduction is terminated, the reaction mixture is cooled to 0°C and there are added thereto 1.65 liters of 1N NaOH. The reaction mixture is then filtered out and the mother liquor is discarded. The resulting filtrate which is a mixture of iron slimes and the desired product is treated twice with three liters of acetone at reflux. After each treatment the mixture is filtered and the combined filtrates are concentrated under a vacuum to produce a residual volume of 1.5 liters which is then diluted with three liters of ice water in order to precipitate the 2-chloro-5-amino anisole. After filtering, there are obtained 669 grams of the desired product which melts at 79°C.

THIRD STEP

Preparation of 2-chloro-5-aminophenol 4.35 Moles (688 grams) of 2-chloro-5-amino anisole are introduced into 3.44 liters of hydrobromic acid ($d = 1.49$) to which has been added 1.38 liters of acetic acid.

The resulting mixture is heated for 3 hours at reflux at which time it is cooled to 0°C. The 2-chloro-5-aminophenol hydrobromide that has precipitated is then filtered, introduced into 3 liters of ice water and neutralized with concentrated ammonia so as to precipitate 2-chloro-5-aminophenol. The desired product which is then filtered to provide a yield of 495 g exhibits, after drying, a melting point of 160°C.

FOURTH STEP

Preparation of 2-chloro-5-acetaminophenol 0.05 Mole (7.17 grams) of 2-chloro-5-aminophenol is dissolved in 21 cc of dioxane at 75°C. There is then added, with agitation, 0.05 mole (5.1 grams) of acetic anhydride. At the end of this addition, the reaction medium is maintained for 10 minutes at 70°C and then cooled. The raw product which has crystallized in then filtered and recrystallized in a hydroalcoholic medium. It exhibits a melting point of 212°C.

| Analysis | Calculated for $C_8H_8NClO_2$ | Found | |
|---|---|---|---|
| C% | 51.75 | 51.74 | 51.75 |
| H% | 4.31 | 4.44 | 4.46 |
| N% | 7.55 | 7.57 | 7.68 |
| Cl% | 19.12 | 19.01 | 19.27 |

2-fluoro-5-acetamino phenol is prepared in a similar manner.

EXAMPLES OF USE

Example 1

The following dye composition is prepared:

| | |
|---|---|
| Dihydrochloride of 2,6-dimethyl-3-methoxy paraphenylenediamine | 0.78 g |
| 2-chloro-5-acetylaminophenol | 0.65 g |
| Ethanol (95°) | 40 g |
| Ammonia (22°Be) q.s.p. | pH = 6 |
| Water, q.s.p. | 100 g |

To this solution there are added 70 grams of $H_2O_2$ (20 volumes). The resulting mixture is then applied for 20 minutes at ambient temperature to bleached hair. After rinsing and shampooing, there is obtained a light green coloration with golden glints.

Example 2

The following dye composition is prepared:

| | |
|---|---|
| Dihydrochloride of 2,5-dimethyl paraphenylenediamine | 1.20 g |
| 2-chloro-5-acetylaminophenol | 0.46 g |
| 7-hydroxy-phenomorpholine | 0.40 g |
| 1-ɣamino propylamino anthraquinone | 0.15 g |
| Nitrometaphenylenediamine | 0.10 g |
| Ethanol (95°) | 30 g |
| Ammonia (22° Be) q.s.p. | pH = 8.5 |
| Water, q.s.p. | 100 g |

To this solution there are added 100 grams of $H_2O_2$ (20 volumes). The resulting mixture is then applied for a period of 20 minutes at 25°C to 95% naturally white hair. After rinsing and shampooing there is obtained a bronze coloration with mordore glints.

Example 3

The following dye composition is prepared:

| | |
|---|---|
| Ammonium salt of 4-amino-N,N-(ethyl, β-sulfoethyl) aniline | 1.29 g |
| 2-chloro-5-acetylaminophenol | 0.92 g |
| Quaternary copolymer of vinyl-pyrrolidone (average molecular weight 100,000) sold under the mark "GAFQUATE 734" | 10 g |
| Triethanolamine, q.s.p. | pH = 9 |
| Water, q.s.p. | 100 g |

To this solution there are added 70 grams of $H_2O_2$ (20 volumes). The resulting mixture is then applied for a period of 25 minutes at ambient temperature to bleached hair. After rinsing and shampooing there is obtained a pearly light emerald green coloration.

Example 4

The following dye composition is prepared:

| | |
|---|---|
| Sulphate of N-[(4'-amino) phenyl] piperidine | 0.45 g |
| 2-chloro-5-acetylaminophenol | 0.36 g |
| Diethanolamide of fatty acid of coco | 10 g |
| Ammonia (22° Be) q.s.p. | pH = 10 |
| Water, q.s.p. | 100 g |

To this solution there are added 100 grams of a 0.90% aqueous solution of ammonium persulfate. The resulting mixture is then applied for a period of 20 minutes at 30°C to 95% naturally white hair. After rinsing and shampooing there is obtained a silvery almond green coloration.

Example 5

The following dye composition is prepared:

| | |
|---|---|
| N-[(4'-amino) phenyl] morpholine | 0.44 g |
| 2-chloro-5-acetylaminophenol | 0.47 g |
| Polymer of acrylic acid (average molecular weight between 2 and 3 million) | 4 g |
| Ammonia (22° Be) q.s.p | pH = 7 |
| Water, q.s.p. | 100 g |

To this solution there are added 100 grams of $H_2O_2$ (20 volumes). The resulting mixture is then applied for a period of 25 minutes at ambient temperature to 95% naturally white har. After rinsing and shampooing there is obtained a metallic gray-blue coloration.

Example 6

The following dye composition is prepared:

| | |
|---|---|
| Dihydrochloride of 3-methyl-4-amino-N,N-(ethyl, β-piperidinoethyl) aniline | 0.20 g |
| 2-chloro-5-acetylaminophenol | 0.28 g |
| Butylglycol | 5 g |
| Lauryl alcohol oxyethylenated with 10.5 moles of ethylene oxide | 5 g |
| Ammonia (22° Be) q.s.p. | pH = 9 |
| Water, q.s.p. | 100 g |

To this solution there are added 70 grams of $H_2O_2$ (20 volumes). The resulting mixture is then applied for a period of 30 minutes at ambient temperature to 95% naturally white hair. After rinsing and shampooing there is obtained an emerald green coloration.

Example 7

The following dye composition is prepared:

| | |
|---|---|
| Chloroparatoluylenediamine | 1.44 g |
| 2-chloro-5-acetylaminophenol | 1.86 g |
| Carboxymethylcellulose | 10 g |
| Ammonia (22° Be) | pH = 9 |
| Water, q.s.p. | 100 g |

To this solution there are added 100 grams of a 2.28% solution of ammonium persulphate. The resulting mixture is then applied for a period of 15 minutes to 95% naturally white hair at ambient temperature. After rinsing and shampooing, there is obtained a light beige-gray coloration.

Example 8

The following dye composition is prepared:

| | |
|---|---|
| Dihydrochloride of paratoluylen diamine | 0.80 g |
| 2-bromo-5-acetylaminophenol | 0.92 g |
| Diethanolamide of fatty acid of coco | 10 g |
| Ammonia (22° Be) q.s.p. | pH = 9.5 |
| Water, q.s.p. | 100 g |

To this solution there are added 50 grams of $H_2O_2$ (20 volumes). The resulting mixture is then applied for a period of 30 minutes at ambient temperature to 95% naturally white hair. After rinsing and shampooing there is obtained a strong kentia green coloration.

Example 9

The following dye composition is prepared:

| | |
|---|---|
| 4-amino-N,N-(ethyl, carbamylmethyl) aniline | 1.15 g |
| 2-bromo-5-acetylaminophenol | 1.38 g |
| Lauryl alcohol oxyethylenated with 10.5 moles of ethylene oxide | 5 g |
| Butylglycol | 5 g |
| Triethanolamine, q.s.p. | pH = 8.5 |
| Water, q.s.p. | 100 g |

To this solution there are added 75 grams of $H_2O_2$ (20 volumes). The resulting mixture is then applied for a period of 20 minutes at ambient temperature to 95% naturally white hair. After rinsing and shampooing there is obtained a silvery eucalyptus green coloration.

Example 10

The following dye composition is prepared:

| | |
|---|---|
| Dihydrochloride of paratoluylenediamine | 0.59 g |
| 2-chloro-5-acetylaminophenol | 0.46 g |
| Ammonia (22° Be) q.s.p. | pH = 10 |
| Water, q.s.p. | 100 g |

To this solution there are added 100 grams of $H_2O_2$ (20 volumes). The resulting mixture is then applied for a period of 20 minutes at 25°C to 95% naturally white hair. After rinsing and shampooing there is obtained a petroleum coloration.

Example 11

The following dye composition is prepared:

| | |
|---|---|
| Dihydrochloride of 2,5-diaminopyridine | 0.36 g |
| 2-bromo-5-acetylaminophenol | 0.46 g |
| Ethanol (95°) | 30 g |
| Water, q.s.p. | 100 g |
| Ammonia (22° Be) q.s.p. | pH = 8 |

To this solution there are added 80 grams of $H_2O_2$ (20 volumes). The resulting mixture is then applied for a period of 20 minutes at 20°C to 95% naturally white hair. After rinsing and shampooing, there is obtained a salmon beige coloration.

Example 12

The following dye composition is prepared:

| | |
|---|---|
| Dihydrochloride of N,N-dimethylparaphenylenediamine | 0.52 g |
| Metaaminophenol | 0.14 g |
| 2-chloro-5-acetylaminophenol | 0.23 g |
| Nitroparaphenylenediamine | 0.05 g |
| Sodium lauryl sulphate with 19% of the starting alcohol being oxyethylenated | 20 g |
| Ethylenediamine tetraacetic acid | 0.2 g |
| Sodium bisulfite (40% solution) | 1 g |
| Ammonia (22° Be) | 10 g |
| Water, q.s.p. | 100 g |

The pH of the solution is equal to 10.2. To this solution having a pH of 10.2 there is added an equal volume of $H_2O_2$ (20 volumes). The resulting mixture is then applied for a period of 20 minutes at 25°C to 95% naturally white hair. After rinsing and shampooing, there is obtained a steel-gray coloration with light violet glints. By the term "sodium lauryl sulphate with 19% of the starting alcohol being oxyethylenated" is meant a mixture constituted by 19% of lauryl alcohol oxyethylenated with 2 moles of ethylene oxide and 81% of the sodium sulfate salt of this same oxyethylenated alcohol.

Example 13

The following dye composition is prepared:

| | |
|---|---|
| 2-methyl-4-amino-N,N-(ethyl, carbamylmethyl) aniline | 1.03 g |
| 2-chloro-5-acetylaminophenol | 0.96 g |
| Ammonia (22° Be) q.s.p. | pH = 9 |
| Water, q.s.p. | 100 g |

To this solution there is added an equal weight of $H_2O_2$ (20 volumes). The resulting mixture is then applied for a period of 10 minutes at ambient temperature to 95% naturally white hair. After rinsing and shampooing, there is obtained an emerald green coloration.

Example 14

The following dye composition is prepared:

| | |
|---|---|
| Paraaminophenol | 0.54 g |
| 2-chloro-5-acetyl aminophenol | 0.72 g |
| 3-methyl-4-hydroxy-6,4'-diaminodiphenylamine | 0.25 g |
| Quaternary copolymer of vinyl-pyrrolidone (average molecular weight 100,000) sold under the mark "GAFQUATE 734" | 10 g |
| Ethanol (95°) | 30 g |
| Triethanolamine, q.s.p. | pH = 9 |
| Water, q.s.p. | 100 g |

To this solution there is added an equal weight of $H_2O_2$ (20 volumes). The resulting mixture is then applied for a period of 30 minutes at 25°C to 95% naturally white hair. After rinsing and shampooing there is obtained a mahogany coloration.

Example 15

The following dye composition is prepared:

| | |
|---|---|
| Monohydrochloride of 3-methyl-4-amino-N,N-diethylaniline | 2.14 g |
| 2-bromo-5-acetylaminophenol | 2.30 g |
| Lauryl alcohol oxyethylenated with 10.5 moles of ethylene oxide | 5 g |
| Butylglycol | 5 g |
| Ammonia (22° Be) q.s.p. | pH = 9 |
| Water, q.s.p. | 100 g |

To this solution there are added 100 grams of a 4.4% solution of ammonium persulfate. The resulting mixture is then applied for a period of 10 minutes at ambient temperature to 95% naturally white hair. After rinsing and shampooing there is obtained metallic gray-green coloration.

Example 16

The following dye composition is prepared:

| | |
|---|---|
| 4-amino-N,N-di-(β-hydroxyethyl) aniline | 2.10 g |
| 2-bromo-5-acetylaminophenol | 2.30 g |
| Carboxymethylcellulose | 10 g |
| Ammonia (22° Be) q.s.p. | pH = 7.5 |
| Water, q.s.p. | 100 g |

To this solution there are added 75 grams of $H_2O_2$ (20 volumes). The resulting mixture is then applied for a period of 25 minutes at ambient temperature to 95% naturally white hair. After rinsing and shampooing there is obtained an intense petroleum green coloration.

Example 17

The following dye composition is prepared:

| | |
|---|---|
| Dihydrochloride of 2,6-dimethyl-3-methoxy paraphenylenediamine | 3.4 |
| 2-bromo-5-acetylaminophenol | 3.4 |
| Lauryl alcohol oxyethylenated with 10.5 moles of ethylene oxide | 12 g |
| Ammonia (22° Be) q.s.p. | pH = 8.5 |
| Water, q.s.p. | 100 g |

To this solution there are added 100 grams of $H_2O_2$ (20 volumes). The resulting mixture is then applied for a period of 25 minutes at ambient temperature to 95% naturally white hair. After rinsing and shampooing, there is obtained a very luminous green coloration.

Example 18

The following dye composition is prepared:

| | |
|---|---|
| Trihydrochloride of 4-amino-N,N-(ethyl, β-piperidinoethyl) aniline | 0.10 g |
| 2-bromo-5-acetylaminophenol | 0.06 g |
| Ethanol (95°) | 25 g |
| Ammonia (22° Be) q.s.p. | pH = 9.5 |
| Water, q.s.p. | 100 g |

To this solution there are added 100 grams of a 0.10% aqueous solution of ammonium persulfate. The resulting mixture is then applied for a period of 20 minutes at ambient temperature to bleached hair. After rinsing and shampooing there is obtained a light silvery blue coloration.

Example 19

The following dye composition is prepared:

| | |
|---|---|
| Dihydrochloride of 2,6-dimethyl-3-methoxy paraphenylenediamine | 0.59 g |
| 2-chloro-5-acetyl aminophenol | 0.46 g |
| Nitrometaphenylenediamine | 0.10 g |
| 1-γ-aminopropylamino anthraquinone | 0.10 g |
| Ethanol (95°) | 25 g |
| Ammonia (22° Be) q.s.p. | pH = 8 |
| Water, q.s.p. | 100 g |

To this solution there is added an equal volume of $H_2O_2$ (20 volumes). The resulting mixture is then applied for a period of 20 minutes at ambient temperature to 95% naturally white hair. After rinsing and shampooing there is obtained a deep golden blonde coloration.

Example 20

The following dye composition is prepared:

| | |
|---|---|
| Paraaminophenol | 0.54 g |
| 2-chloro-5-acetylaminophenol | 0.92 g |
| Ammonia (22° Be) q.s.p. | pH = 9.5 |
| Water, q.s.p. | 100 g |

To this solution there are added 100 grams of a 2.28% solution of ammonium persulfate. The resulting mixture is then applied for a period of 30 minutes at ambient temperature to 95% naturally white hair. After rinsing and shampooing there is obtained a hazel coloration.

Example 21
The following dye composition is prepared:

| | |
|---|---|
| Hydrochloride of 2-chloro-4-aminophenol | 0.45 g |
| 2-chloro-5-acetylaminophenol | 0.46 g |
| Sodium lauryl sulphate with 19% of the starting alcohol being oxyethylenated | 20 g |
| Ethylenediamine tetraacetic acid | 0.2 g |
| Sodium bisulfite (40% solution) | 1 g |
| Ammonia (22° Be) | 10 g |
| Water, q.s.p. | 100 g |

To this solution having a pH of 10.3 there are added 100 grams of $H_2O_2$ (20 volumes). The resulting mixture is then applied for a period of 20 minutes at ambient temperature to bleached hair. After rinsing and shampooing there is obtained an anise coloration.

Example 22
The following dye composition is prepared:

| | |
|---|---|
| Dihydrochloride of methoxy paraphenylenediamine | 1.12 g |
| 2-bromo-5-acetylaminophenol | 1.15 g |
| Ethanol (95°) | 30 g |
| Ammonia (22° Be) q.s.p. | pH = 10 |
| Water, q.s.p. | 100 g |

To this solution there are added 80 grams of $H_2O_2$ (20 volumes). The resulting mixture is then applied for a period of 20 minutes at ambient temperature to hair having a natural red chestnut coloration. After rinsing and shampooing, there is obtained a bronze green coloration with moredore glints.

Example 23
The following dye composition is prepared:

| | |
|---|---|
| Hydrochloride of 2,6-dimethyl-4-aminophenol | 1.13 g |
| 2-chloro-5-acetylaminophenol | 0.56 g |
| Diethanolamide of fatty acids of coco | 10 g |
| Ammonia (22° Be) q.s.p. | pH = 9 |
| Water, q.s.p. | 100 g |

To this solution there are added 25 grams of $H_2O_2$ (20 volumes). The resulting mixture is then applied for a period of 20 minutes at ambient temperature to 95% naturally white hair. After rinsing and shampooing there is obtained a rose champagne coloration.

Example 24
The following dye composition is prepared:

| | |
|---|---|
| Hydrochloride of 2-chloro-4-aminophenol | 0.45 g |
| Metaaminophenol | 0.14 g |
| 2-chloro-5-acetylaminophenol | 0.23 g |
| Sodium lauryl sulphate with 19% of the starting alcohol being oxyethylenated | 20 g |
| Ethylenediamine tetraacetic acid | 0.2 g |
| Sodium bisulfite (40% solution) | 1 g |
| Ammonia (22° Be) | 10 g |
| Water, q.s.p. | 100 g |

The pH of this solution is 10.3. To this solution having a pH of 10.3 there is added an equal weight of $H_2O_2$ (20 volumes). The resulting mixture is then applied for 15 minutes at ambient temperature to bleached hair. After rinsing and shampooing there is obtained an ash blonde coloration.

Example 25
The following dye composition is prepared:

| | |
|---|---|
| Dihydrochloride of para-toluylenediamine | 0.49 g |
| 2-chloro-5-acetylaminophenol | 0.23 g |
| Dihydrochloride of 2,4-diamino anisole | 0.13 g |
| Resorcin | 0.06 g |
| Sodium lauryl sulphate with 19% of the starting alcohol being oxyethylenated | 20 g |
| Ethylenediamine tetraacetic acid | 0.2 g |
| Ammonia (22° Be) | 10 g |
| Water, q.s.p. | 100 g |

To this solution, having a pH of 10 there are added 100 grams of $H_2O_2$ (20 volumes). The resulting mixture is then applied for a period of 15 minutes to bleached hair at ambient temperature. After rinsing and shampooing, a slate gray-blue coloration is obtained.

Example 26
The following dye composition is prepared:

| | |
|---|---|
| Dihydrochloride of 2,6-dimethyl-3-methoxy paraphenylenediamine | 0.52 g |
| 2-bromo-5-acetylaminophenol | 0.56 g |
| N-[(4'-dimethylamino)phenyl] benzoquinone imine | 0.40 g |
| N-[(4'-hydroxy)phenyl]-2-methyl-5-amino benzoquinone imine | 0.40 g |
| Lauryl alcohol oxyethylenated with 10.5 moles of ethylene oxide | 5 g |
| Butylglycol | 5 g |
| Water, q.s.p. | 100 g |
| Ammonia (22° Be) q.s.p. | pH = 9.7 |

To this solution there are added 80 grams of $H_2O_2$ (20 volumes). The resulting mixture is then applied for a period of 15 minutes at ambient temperatures to 95% naturally white hair. After rinsing and shampooing, there is obtained a cactus green coloration.

Example 27
The following dye composition is prepared:

| | |
|---|---|
| Sulphate of 3-methyl-4-amino-N,N-(ethyl, β-mesylaminoethyl) paraphenylenediamine | 1.36 g |
| 2-chloro-5-acetylaminophenol | 0.93 g |
| Butylglycol | 5 g |
| Lauryl alcohol oxyethylenated with 10.5 moles of ethylene oxide | 5 g |
| Triethanolamine q.s.p. | pH = 5.5 |
| Water, q.s.p. | 100 g |

To this solution there are added 100 grams of 10% aqueous solution of urea peroxide. The resulting mixture is then applied for a period of 20 minutes at ambient temperature to 95% naturally white hair. After rinsing and shampooing, there is obtained a silvery gray-green coloration.

What is claimed is:

1. A dye composition for keratinic fibers comprising an aqueous or hydroalcoholic solution of
   a. at least one oxidation base being an aromatic or heterocyclic compound carrying either two amino groups or one amino group and one hydroxy group, fixed in para position relative to each other on the aromatic or heterocyclic nucleus of said compound, said oxidation base being in the form of a free base or in the form of an acid addition salt thereof; and
   b. at least one coupler of the formula:

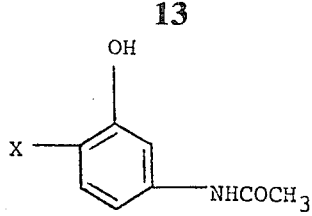

wherein X represents fluorine, chlorine or bromine, said coupler being present in an amount of 0.5 - 3.5 percent based on the total weight of said composition and the molar ratio of said oxidation base to said coupler being between 2.5:1 and 1:2.5.

2. The composition of claim 1 wherein said oxidation base is a paraphenylenediamine in the form of a free base or in the form of a salt.

3. The composition of claim 2 wherein said paraphenylenediamine is selected from the group consisting of: paraphenylenediamine, paratoluylenediamine, methoxyparaphenylenediamine, chloroparaphenylenediamine, 2,6-dimethyl paraphenylenediamine, 2,5-dimethyl paraphenylenediamine, 2-methyl-5-methoxy paraphenylenediamine, 2,6-dimethyl-5-methoxy paraphenylenediamine, N,N-dimethyl paraphenylenediamine, 3-methyl-4-amino-N,N-diethylaniline, N,N-di-($\beta$-hydroxyethyl) paraphenylenediamine, 3-methyl-4-amino-N,N-di($\beta$-hydroxyethyl) aniline, 3-chloro-4-amino-N,N-di($\beta$-hydroxyethyl) aniline, 4-amino-N,N-(ethyl, carbamylmethyl) aniline, 3-methyl-4-amino-N,N-(ethyl, carbamylmethyl) aniline, 4-amino-N,N-(ethyl, $\beta$-piperidinoethyl) aniline, 3-methyl-4-amino-N,N-(ethyl, $\beta$-piperidinoethyl) aniline, 4-amino-N,N-(ethyl, $\beta$-morpholinoethyl) aniline, 3-methyl-4-amino-N,N-(ethyl, $\beta$-morpholinoethyl) aniline, 4-amino-N,N-(ethyl, $\beta$-acetylamino ethyl) aniline, 3-methyl-4-amino-N,N-(ethyl, $\beta$-acetylamino ethyl) aniline, 4-amino-N,N-(ethyl, $\beta$-mesylaminoethyl) aniline, 3-methyl-4-amino-N,N-(ethyl, $\beta$-mesylaminoethyl) aniline, 4-amino-N,N-(ethyl, $\beta$-sulfoethyl) aniline, 3-methyl-4-amino-N,N-(ethyl, $\beta$-sulfoethyl) aniline, N-[(4'-amino) phenyl] morpholine and N-[(4'-amino) phenyl] piperidine.

4. The composition of claim 1 wherein said oxidation base is a paraaminophenol in the form of a free base or in the form of a salt.

5. The composition of claim 4 wherein said paraaminophenol is selected from the group consisting of: paraaminophenol, 2-methyl-4-amino phenol, 3-methyl-4-amino phenol, 2-chloro-4-amino phenol, 3-chloro-4-amino phenol, 2,6-dimethyl-4-amino phenol, 3,5-dimethyl-4-amino phenol, 2,3-dimethyl-4-amino phenol and 2,5-dimethyl-4-amino phenol.

6. The composition of claim 1 wherein said oxidation base is selected from the group consisting of 2,5-diamino pyridine, 2-hydroxy-5-amino pyridine and salts thereof.

7. The composition of claim 1 which also includes at least one additional coupler.

8. The composition of claim 7 wherein said additional coupler is selected from the group consisting of resorcin, metaaminophenol, 2,4-diamino anisole, 7-hydroxy-phenomorpholine, 2-methyl-5-amino phenol, 2,6-dimethyl amino phenol, 2-chloro-5-amino phenol, 3-amino-4-methoxy phenol, 2,6-dimethyl-5-ureidophenol, 3-acetylamino phenol, 2-methyl-5-ureido phenol, 2-methyl-5-acetylamino phenol and a pyrazolone.

9. The composition of claim 1 which also includes a dye selected from the group consisting of anthraquinone, nitrobenzene, indamine, indophenol, and indoaniline dye.

10. The composition of claim 1 which also includes a leucoderivative of indamine, a leucoderivative of indophenol or a leucoderivative of indoaniline.

11. The composition of claim 1 wherein said hydroalcoholic solution contains a lower alkanol.

12. The composition of claim 1 which also contains one or more of a glycol, wetting agent, thickening agent, vinyl pyrrolidone polymer, acrylic acid polymer, complexing agent and reducing agent.

13. The composition of claim 1 having a pH between 5 and 11.

14. A process for dyeing human hair consisting essentially of applying an effective amount of a mixture of an oxidizing agent and the dye composition of claim 1 to the hair and rinsing, washing and drying the hair.

15. The process of claim 14 wherein said oxidizing agent is selected from the group consisting of $H_2O_2$, urea peroxide and a persalt.

* * * * *